US009504594B2

(12) United States Patent
Schmid et al.

(10) Patent No.: US 9,504,594 B2
(45) Date of Patent: Nov. 29, 2016

(54) INFANT HIP JOINT POSITIONING DEVICE AND ASSOCIATED METHODS

(75) Inventors: William R. Schmid, Plymouth, MN (US); Charles Turner Price, Winter Park, FL (US); Dawn Griffin, Wayzata, MN (US)

(73) Assignee: Halo Innovations, Inc., Minnetonka, MN (US)

( * ) Notice: Subject to any disclaimer, the term of this patent is extended or adjusted under 35 U.S.C. 154(b) by 203 days.

(21) Appl. No.: 13/638,246

(22) PCT Filed: Mar. 22, 2011

(86) PCT No.: PCT/US2011/029359
§ 371 (c)(1),
(2), (4) Date: Sep. 28, 2012

(87) PCT Pub. No.: WO2011/123287
PCT Pub. Date: Oct. 6, 2011

(65) Prior Publication Data
US 2013/0023810 A1  Jan. 24, 2013

Related U.S. Application Data

(60) Provisional application No. 61/319,302, filed on Mar. 31, 2010, provisional application No. 61/433,412, filed on Jan. 17, 2011.

(51) Int. Cl.
*A61F 5/01* (2006.01)
*A61H 1/02* (2006.01)
(Continued)

(52) U.S. Cl.
CPC .............. *A61F 5/0193* (2013.01); *A41D 13/00* (2013.01); *A41D 13/05* (2013.01);
(Continued)

(58) Field of Classification Search
CPC .......... A61F 5/00; A61F 5/01; A61F 5/0102; A61F 5/0193; A61H 1/00; A61H 1/02; A61H 1/0237; A61H 1/0244; A61H 1/0255; A41D 1/00; A41D 1/08; A41D 1/088; A41D 13/00; A41D 13/05; A41D 13/0506

USPC ........... 128/98.1, 846, 869, 882, 891; 602/5, 602/23, 24, 25; 604/358, 385.25, 385.31, 604/393; 2/466, 69, 69.5, 70, 73, 75, 78.1, 2/78.2, 78.4, 80, 109, 111, 400–402
See application file for complete search history.

(56) References Cited

U.S. PATENT DOCUMENTS 2,935,984 A * 5/1960 Kerr ................................. 602/24
3,730,177 A * 5/1973 Thum ............................. 602/24
(Continued)

FOREIGN PATENT DOCUMENTS

| GB | 2188240 | 9/1987 |
|----|---------|--------|
| JP | 34-7396 | 8/1959 |

(Continued)

OTHER PUBLICATIONS

Japanese Office Action issued in Japanese Application No. 2013-502643, mail date Apr. 9, 2015, with English translation (9 pages).
(Continued)

*Primary Examiner* — Ophelia A Hawthorne
(74) *Attorney, Agent, or Firm* — Hamre, Schumann, Mueller & Larson, P.C.

(57) ABSTRACT

A device and method are provided for positioning an infant's hips, and for maintaining the hip joint in a physiological position, during early months of life. The hip-positioning device includes a flexible base having a pair of opposed, outwardly extending side portions. The side portions are dimensioned for supporting thighs of an infant at an acute angle greater than zero relative to a dorsal plane of the infant, with knees of the infant in a flexed position. The base further has a downwardly extending, generally central portion that is adapted for positioning between the infant thighs and dimensioned for retaining the infant thighs in an abducted position. The device additionally includes an element for retaining the base on the infant.

9 Claims, 13 Drawing Sheets

(51) Int. Cl.
  *A41D 13/00* (2006.01)
  *A61H 1/00* (2006.01)
  *A41D 13/05* (2006.01)
  *A61F 5/00* (2006.01)
  *A41D 1/08* (2006.01)
  *A41D 1/00* (2006.01)

(52) U.S. Cl.
  CPC ............ *A41D 13/0506* (2013.01); *A61F 5/00* (2013.01); *A61F 5/0102* (2013.01); *A61H 1/00* (2013.01); *A61H 1/02* (2013.01); *A61H 1/0237* (2013.01); *A61H 1/0244* (2013.01); *A61H 1/0255* (2013.01); *A41D 1/00* (2013.01); *A41D 1/08* (2013.01); *A41D 1/088* (2013.01)

(56) References Cited

U.S. PATENT DOCUMENTS

| | | | |
|---|---|---|---|
| 3,759,252 A | | 9/1973 | Berman |
| 3,815,589 A | * | 6/1974 | Bosley ........................... 602/24 |
| 4,135,504 A | * | 1/1979 | Spann ............................ 602/24 |
| 4,393,865 A | * | 7/1983 | Lambert ............... A61F 5/0193 602/24 |
| 4,574,790 A | | 3/1986 | Wellershaus |
| D287,406 S | * | 12/1986 | Dixon .......................... D24/190 |
| 4,901,710 A | * | 2/1990 | Meyer ............................. 602/24 |
| 4,913,136 A | * | 4/1990 | Chong et al. ................... 602/24 |
| 4,961,737 A | * | 10/1990 | Orlando .................... 604/385.26 |
| 4,964,858 A | | 10/1990 | Livny |
| 5,618,264 A | | 4/1997 | Vasquez |
| 2004/0250338 A1 | * | 12/2004 | Schaefer ............ A41D 13/0506 2/227 |
| 2008/0114319 A1 | * | 5/2008 | Burns et al. ............. 604/385.01 |

FOREIGN PATENT DOCUMENTS

| | | |
|---|---|---|
| JP | 37-21664 U | 8/1962 |
| JP | 51-16142 | 2/1976 |
| JP | 62-253053 | 11/1987 |
| JP | 2-142560 | 5/1990 |
| JP | 10-501146 | 2/1998 |
| JP | 2004-298467 | 10/2004 |
| WO | WO 95/32698 | 12/1995 |

OTHER PUBLICATIONS

Japanese Office Action issued in Japanese Application No. 2013-502643, mail date Dec. 9, 2014, with English translation (11 pages).

* cited by examiner

Normal

Fig. 2B
Prior art

Subluxation

Fig. 2C
Prior art

Low Dislocation

Fig. 2D
Prior art

High Dislocation

INFANT HIP JOINT POSITIONING DEVICE AND ASSOCIATED METHODS

FIELD

The present disclosure relates to orthopedic devices, and, more particularly, to orthopedic devices for stabilizing an infant hip joint.

BACKGROUND

Figure 1:
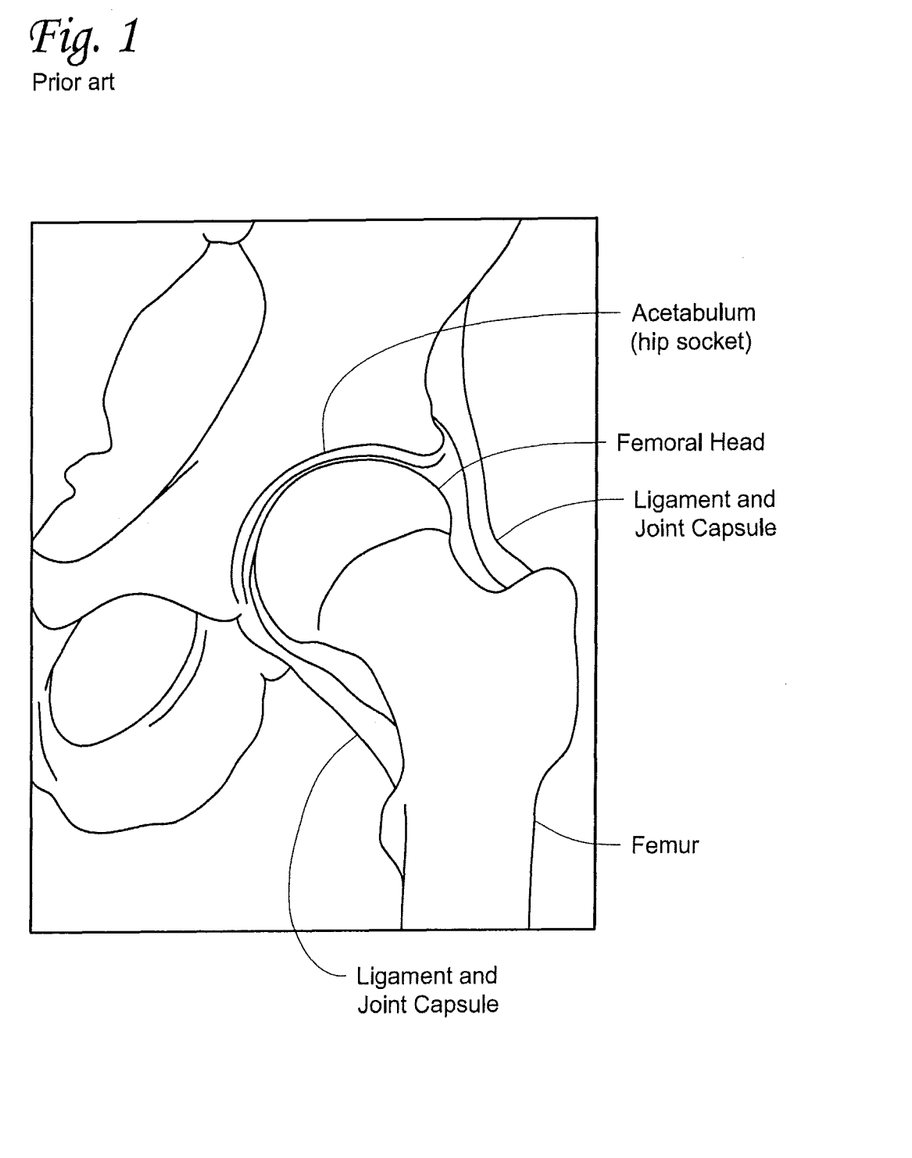
FIG. 1 (prior art) is a diagram of the human hip joint.
Figure 2A:
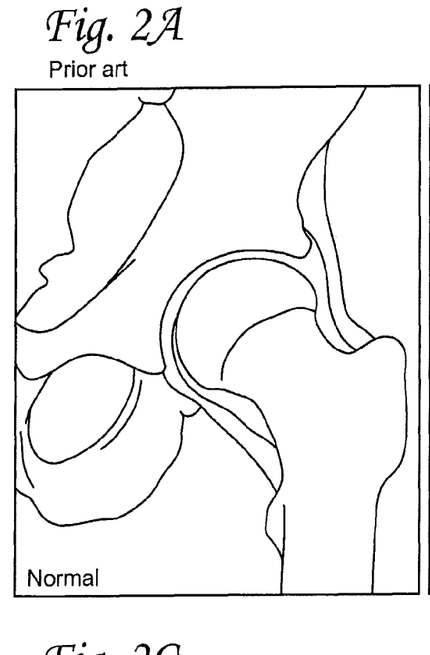
FIGS. 2A-2D (prior art) illustrate various hip joint configurations, including normal (FIG. 2A) and experiencing subluxation (FIG. 2B), low dislocation (FIG. 2C), and high dislocation (FIG. 2D).
Figure 2B:
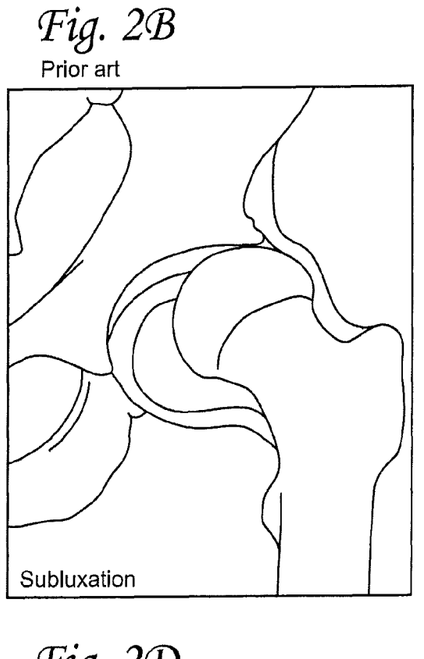
Figure 2C:
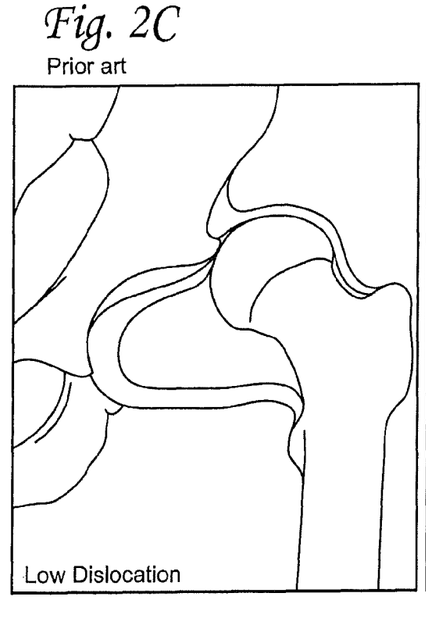
Figure 2D:
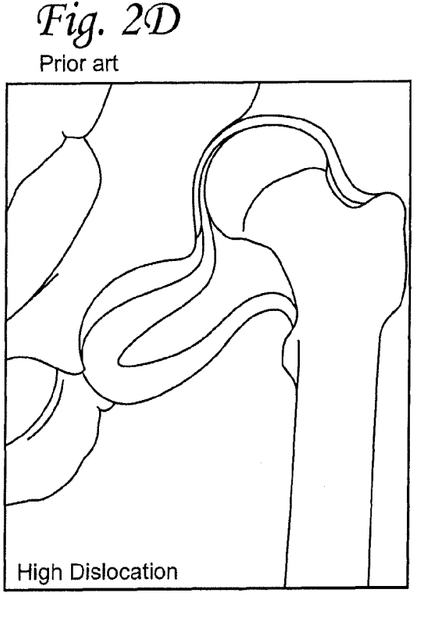

Hip dysplasia is the medical term for instability, or looseness, of the hip joint that affects thousands of children each year. Hip dysplasia occurs when the ball of the hip (called the femoral head) is not properly located in the hip socket (see FIGS. 2A-2D for illustrations of a normal and subluxated and dislocated hip joints). The condition is usually diagnosed in babies and ranges from mild instability to complete dislocation. Approximately one out of every twenty full-term babies has some hip instability, and, of these, 2-3 per 1000 will require treatment. See FIG. 1 for an illustration of the anatomy of the hip.

The frequency is variable depending on gender, race, and other factors, including post-natal positioning. Statistically, girls have a higher incidence of hip dysplasia than boys.

Untreated hip dysplasia is a silent childhood condition that frequently causes disability and arthritis in adults. Hip dysplasia is a hidden condition because it does not cause pain in children, and walking is achieved at the normal age. In spite of the frequency and the potential for life-long disability, there is poor awareness outside the medical profession that this is a common condition. Early diagnosis and simple treatment is the best solution, but some cases go undetected or are difficult to treat when discovered late. Also, many children around the world do not have access to early diagnosis and treatment.

There are a variety of treatments that are used depending on the age of the child and the severity of the condition. Current treatment methods are directed towards detecting and treating persistent instability and complete hip dislocation.

Figure 3A:
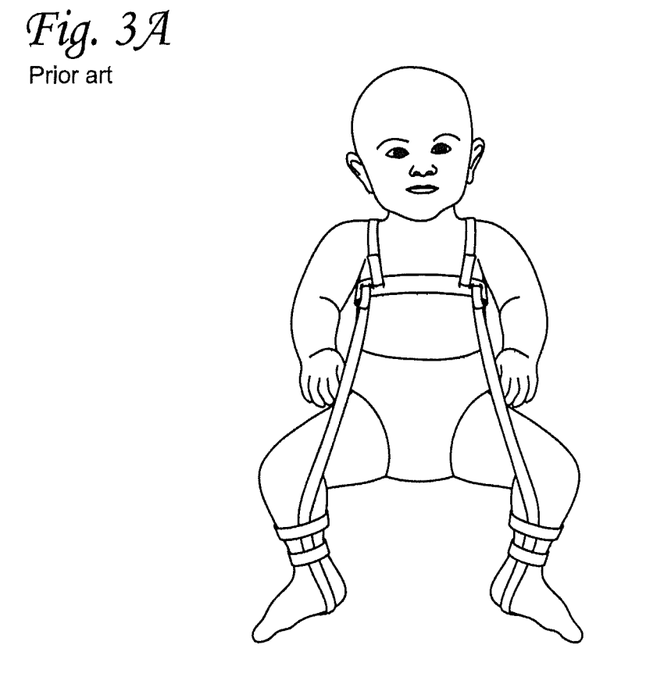
FIGS. 3A and 3B (prior art) are front (FIG. 3A) and rear (FIG. 3B) views of the Pavlik harness.
Figure 3B:
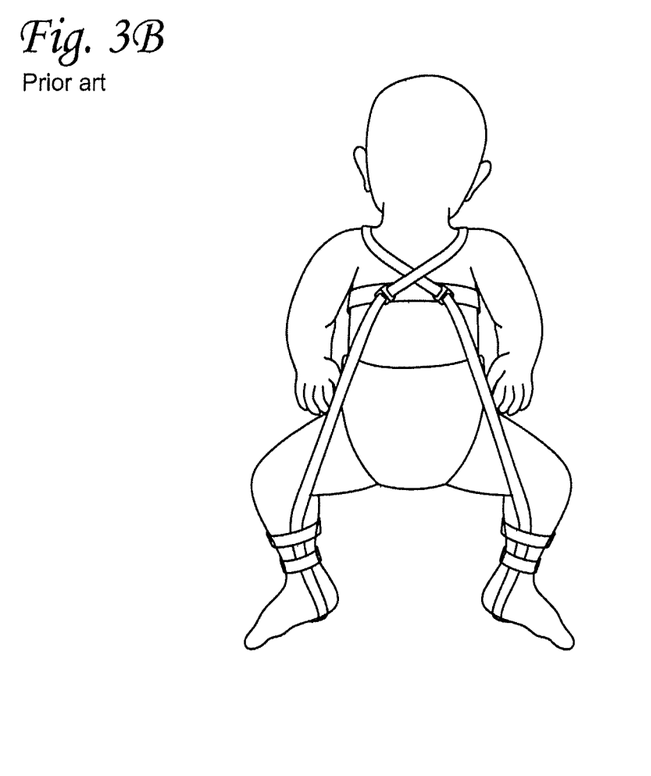

When hip dislocation occurs at the time of birth, the ligaments are stretched and the socket is shallow. Usually, the joint will become normal if the hip can be held in the socket until it becomes stable. Dislocated or unstable hips in newborn infants can usually be held in place by a brace or harness until the ligaments become more stable. There are a wide variety of holding devices available, but the most common ones are the Pavlik Harness (FIGS. 3A and 3B) and various types of devices called fixed abduction braces. There are other types of harnesses and devices that are also used to treat persistent hip instability and dislocation. Most doctors recommend full-time wear for 6-12 weeks, but some doctors allow removal for bathing and diaper changes as long as the legs are spread apart to keep the hips pointed at the socket. After the hips become stable, the brace is worn part-time, usually at night, for another 4-6 weeks. Adverse consequences have also been reported when these treatment devices are used. Therefore, these treatments are reserved for cases with documented and persistent instability or dislocation.

When hip dysplasia or dislocation is diagnosed after several months of age, there are greater changes in the soft tissue and ligaments. Treatment may require closed reduction under general anesthesia and application of a body cast to hold the hip in the socket for several months. Surgery is necessary when closed reduction fails or when the diagnosis is made after walking age.

The longer the hip is out of place, the more difficult it is for the hip to return to normal and the greater the risk of problems from the condition or from necessary treatments.

Although current medical practice is to detect and treat persistent instability and dislocation, there are many children who go undiagnosed by current methods. The efficacy of current screening methods has been questioned as a preventative measure. In 2006, the United States Preventative Health Services Task Force released the conclusion that evidence is insufficient to recommend routine screening for developmental dysplasia of the hip in infants as a means to prevent adverse outcomes.

In spite of efforts at screening, early detection, and specific treatment of hip dysplasia during infancy, there are numerous subtle degrees of dysplasia that lead to adult osteoarthritis of the hip. It has been estimated that subtle forms of hip dysplasia account for 5-10% of all hip replacement surgeries performed in the United States. Mild acetabular dysplasia may be the most common cause of osteoarthritis of the hip in women. Thus it seems that our current diagnosis and treatment methods during infancy and childhood have been insufficient in the prevention of osteoarthritis and disability associated with hip dysplasia.

There is evidence that hip dysplasia is not present in the developing fetus and that the condition occurs at birth or shortly after birth. There is also evidence that infant positioning in the neonatal period with the thighs held together in extension increases the risk of subsequent hip dysplasia. Hip dislocation and dysplasia were common among Navajo Indians who carried their babies on papoose boards with the hips in extension. Hip dislocation and dysplasia were also common in Japan when babies were swaddled tightly with their legs in extension. Both cultures have dramatically reduced the frequency of hip dysplasia by changing their habits for positioning of babies during early infancy. Ethnic groups that nurse and carry their babies with the legs around the torso of the mother have a lower frequency of hip dysplasia and a lower frequency of adult hip arthritis. Thus, post-natal positioning may influence and reduce the frequency of undetected hip dysplasia. Swaddling has recently been re-introduced to the United States and other countries as a method to reduce the frequency of infant colic and fussiness.

It is believed that keeping the infant in a position more akin to that in the womb, i.e., the "frog position," with the legs apart and slightly bent upward at the knee, can prevent immediate and later problems in hip joint development. The normal infant hip has approximately 35° of physiological hip flexion contracture at birth. Extension of the hip and adduction of the thighs together have deleterious effects on hip stability. There are no commercial devices currently available in the USA for maintenance of normal and mildly unstable hips by gentle positioning in a physiological position that encourages hip flexion.

While a number of harnesses and devices known for use in retaining the infant in a proper position for hip joint development, none is known to position the infant's hips in a slightly flexed and abducted physiological position and allow the infant to remain supine, a recommended position for reducing the incidence of sudden infant death syndrome.

SUMMARY

The present disclosure is directed to a device and method for positioning an infant's hips, and for maintaining the hip joint in a healthy physiological positioning even during swaddling or supine positioning. The device maintains the baby's hips in a physiological position without resorting to the extreme positioning associated with braces and harnesses known to be used to treat persistent instability and dislocation. The hip-positioning device comprises a flexible base having a pair of opposed, outwardly extending side portions. The side portions are dimensioned for supporting thighs of an infant so the hips are in slight flexion at an angle greater than zero relative to a dorsal plane of the infant, with knees of the infant in a flexed position and the thighs spread apart in abduction.

The base further has a downwardly extending, generally central portion that is adapted for positioning between the infant thighs and dimensioned for retaining the infant's thighs in an abducted position. The device additionally comprises means for retaining the base on the infant.

A method for positioning an infant's hips comprises positioning an infant in a supine position and placing a device base beneath the infant. A downwardly extending, generally central portion of the base is positioned between the thighs of the infant so as to retain the thighs in an abducted position. Opposed, outwardly extending side portions of the base are positioned beneath the infant's thighs so as to support the thighs at an acute angle greater than zero relative to a dorsal plane of the infant, with knees of the infant in a flexed position. The base is then affixed to the infant to retain the base portions in a predetermined orientation.

DETAILED DESCRIPTION

Figure 4:
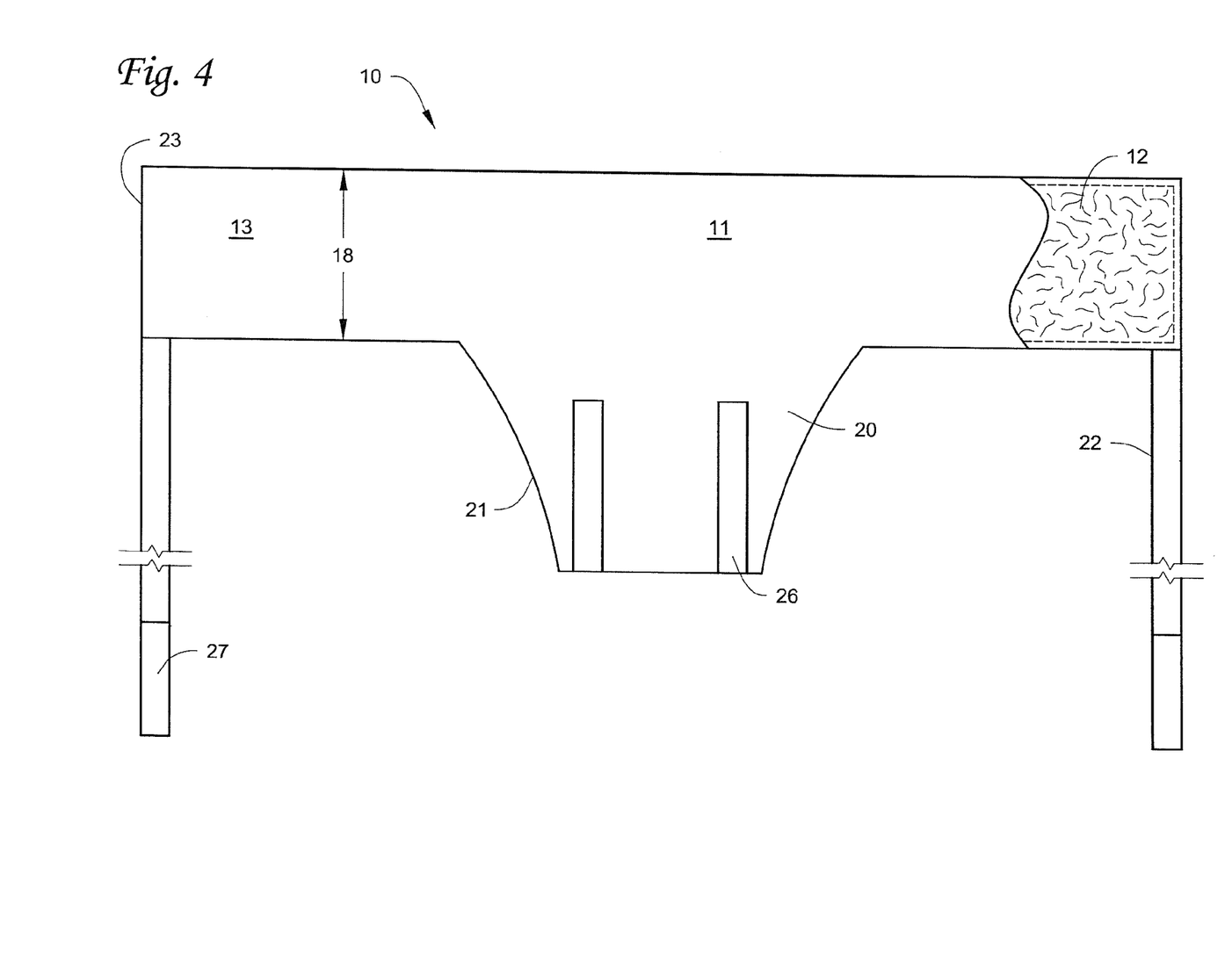
FIG. 4 is a top planar view of a first embodiment of the hip-positioning device of the present disclosure.
Figure 5A:
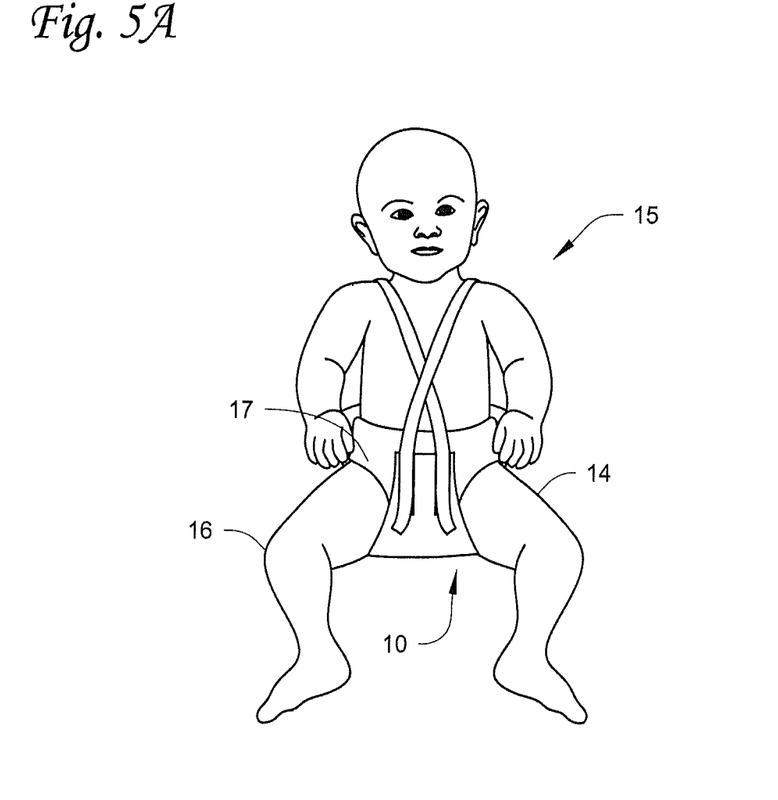
FIGS. 5A and 5B are photographs of the device of FIG. 4 positioned on a doll, in top planar (FIG. 5A) and side (FIG. 5B) views.
Figure 5B:
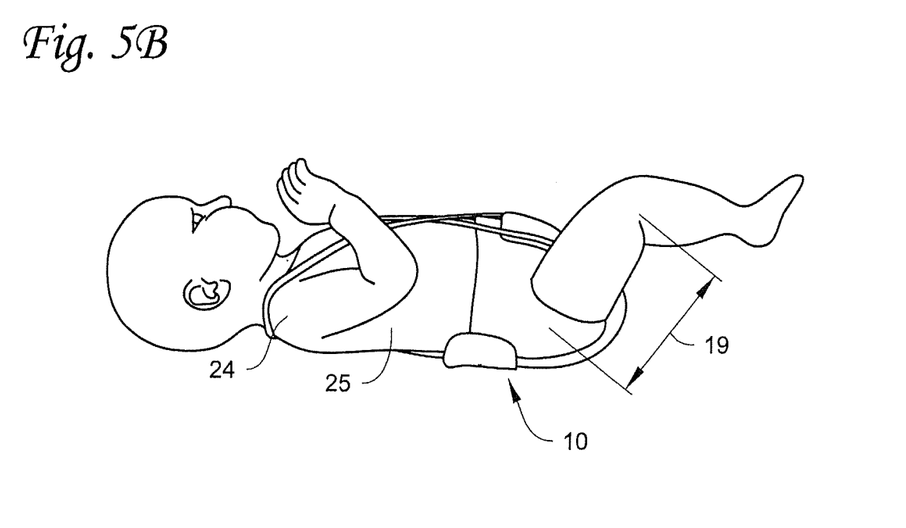

One embodiment of a device 10 for positioning an infant's hips and for maintaining the hip joint in a physiological neonatal position is illustrated in FIGS. 4-5B. The hip-positioning device 10 comprises a flexible base 11. In this embodiment, the base 11 comprises a unitary element having a pliable stuffing 12 therein.

The base 11 has a pair of opposed, outwardly extending side portions 13.

Here, the side portions 13 are illustrated as being substantially rectangular, although this is not intended as a limitation. The side portions 13 are dimensioned for supporting thighs 14 of an infant 15 (here illustrated on a doll) at an acute angle greater than zero relative to a dorsal plane of the infant 15, with knees 16 of the infant 15 in a flexed position. In this embodiment the stuffing 12 in the base 11 is tailored to achieve an optimal amount of elevation and flexion for positioning the infant's hips 17 in a desired orientation. In one example, a height 18 of the side portions 13 is dimensioned less than a knee-to-hip distance 19 on the infant 15.

The base 11 further has a downwardly extending, generally central portion 20 that is adapted for positioning between the infant's thighs 14. The central portion 20 here has a generally trapezoidal shape, although this is not intended as a limitation. Sides 21 of the central portion 20 are slightly arcuate to accommodate the infant's thighs 14 thereagainst.

The central portion 20 is dimensioned for retaining the infant's thighs 14 in an abducted position. In this embodiment, the stuffing 12 in the central portion 20 is sufficient to support the infant's thighs 14 in the desired position.

The device 10 additionally comprises means for retaining the base 11 on the infant 15. In this embodiment the retaining means comprises a pair of opposed straps 22 extending downwardly adjacent ends 23 of the side portions 13.

In use, the base 11 is positioned as shown in FIGS. 5A,5B, with the side portions 13 beneath the infant's thighs 14 and the central portion 20 between the infant's thighs 14. The straps 22 extend over the shoulders 24, are crossed over the torso 25, and are affixed to the central portion 20, for example, via hook-and-loop type fasteners 26,27 on the central portion 20 and straps 22, respectively.

Figure 6:
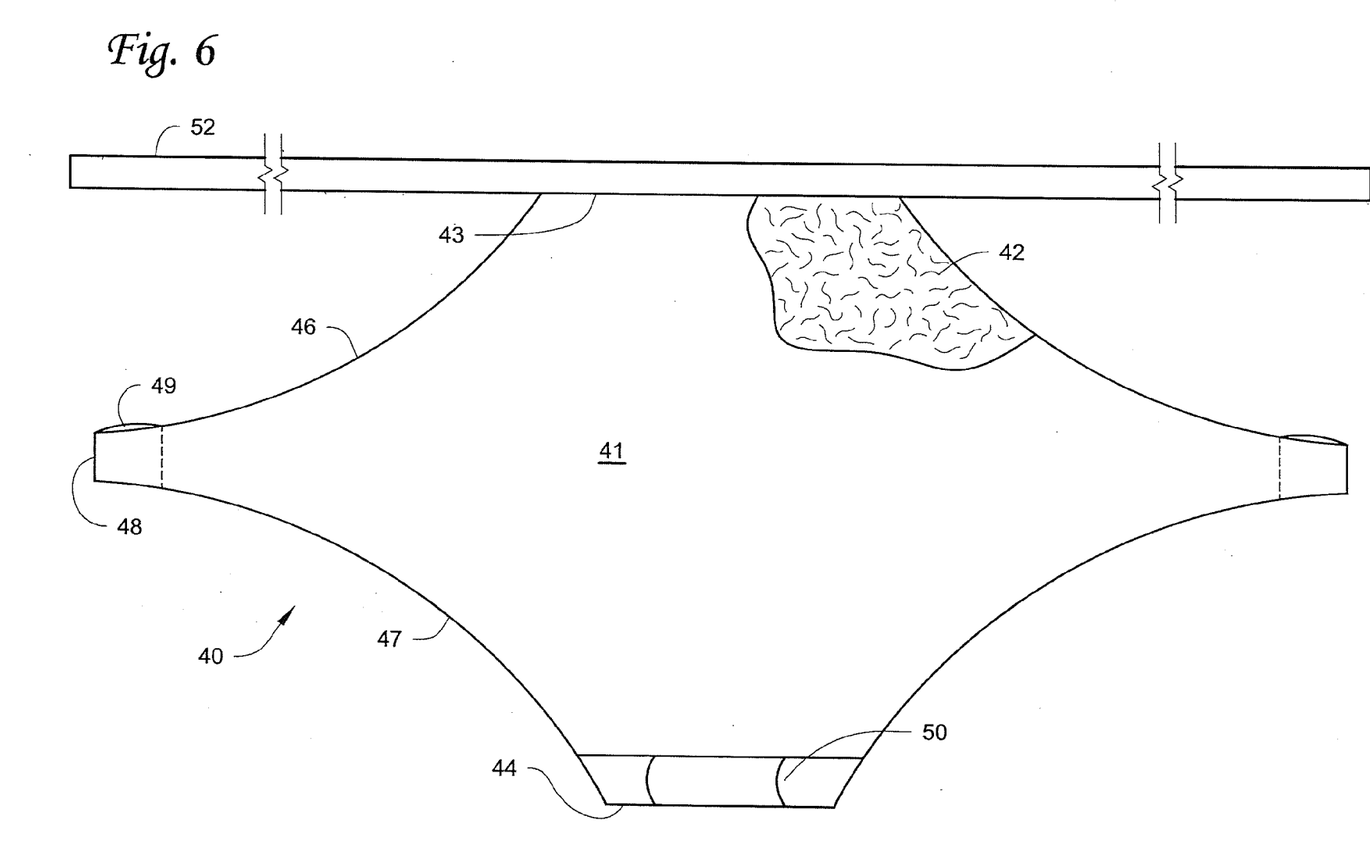
FIG. 6 is a top planar view of a second embodiment of the hip-positioning device of the present disclosure.
Figure 7:
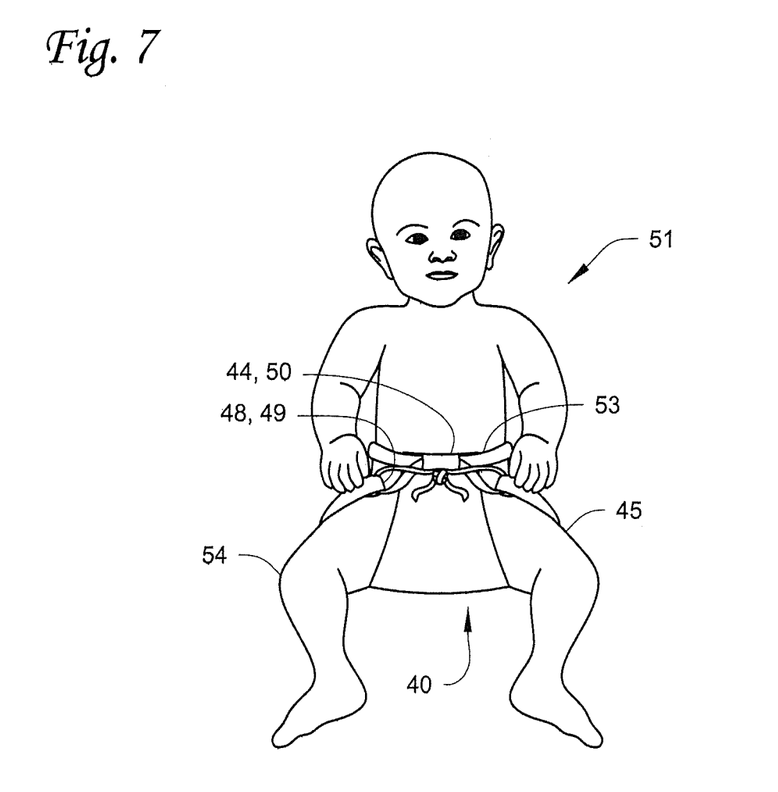
FIG. 7 is a photograph of the device of FIG. 6 positioned on an infant.

Another embodiment of a device 40 for positioning an infant's hips, and for maintaining the hip joint secure, is illustrated in FIGS. 6 and 7. The hip-positioning device 40 comprises a flexible base 41. In this embodiment, the base 41 comprises a unitary element having a pliable stuffing 42 therein.

The base 41 is generally shaped as a truncated diamond, with substantially parallel top 43 and bottom 44 edges. The bottom edge 44 is dimensioned for retaining the infant's thighs 45 in an abducted position. In this embodiment, the stuffing 42 in the base 41 is sufficient to support the infant's thighs 45 in the desired position.

Two arcuate top-side edges 46 extend downwardly from the top edge 43, and two arcuate bottom-side edges 47 extend upwardly from the bottom edge 44. The topside 46 and bottom-side 47 edges are bridged by opposed side ends

48, each of which has an aperture 49 thereadjacent substantially parallel to the respective side end 48.

The bottom edge 44 also has an aperture 50 thereadjacent that is substantially parallel to the bottom edge 44.

The device 40 additionally comprises means for retaining the base 41 on the infant 51. In this embodiment, the retaining means comprises a strap 52 affixed to the base top edge 43, and extending outwardly generally parallel to the top edge 43.

In use, the base 41 is positioned as shown in FIG. 7, with the bottom-side edges 47 and bottom edge 44 wrapped between the infant's thighs 45 and folded upward so that the bottom edge 44 extends to the infant's waist 53. The side ends 48 are wrapped around the infant's thighs 45 and meet generally centrally adjacent the infant's waist 53, with the top-side edges 46 around the infant's waist 53.

The strap 52 extends around the infant's waist 53, through the side end apertures 49 and the bottom edge aperture 50 and affixed together, for example, by tying. The dimensions of the base 41 are adapted for supporting the infant's thighs 45 of at an acute angle greater than zero relative to a dorsal plane of the infant 45, with knees 54 of the infant 51 in a flexed position.

In one example, the devices 10,40 serve to maintain slight flexion at all times, allowing extension to ≥35°. The devices 10,40 also allow greater degrees of flexion than known devices, leaving the knees free but encouraging flexion because of the hip flexion position. The devices 10,40 further block adduction so that hips are maintained in an at least 30° abduction position, while permitting further voluntary abduction.

Figure 8:
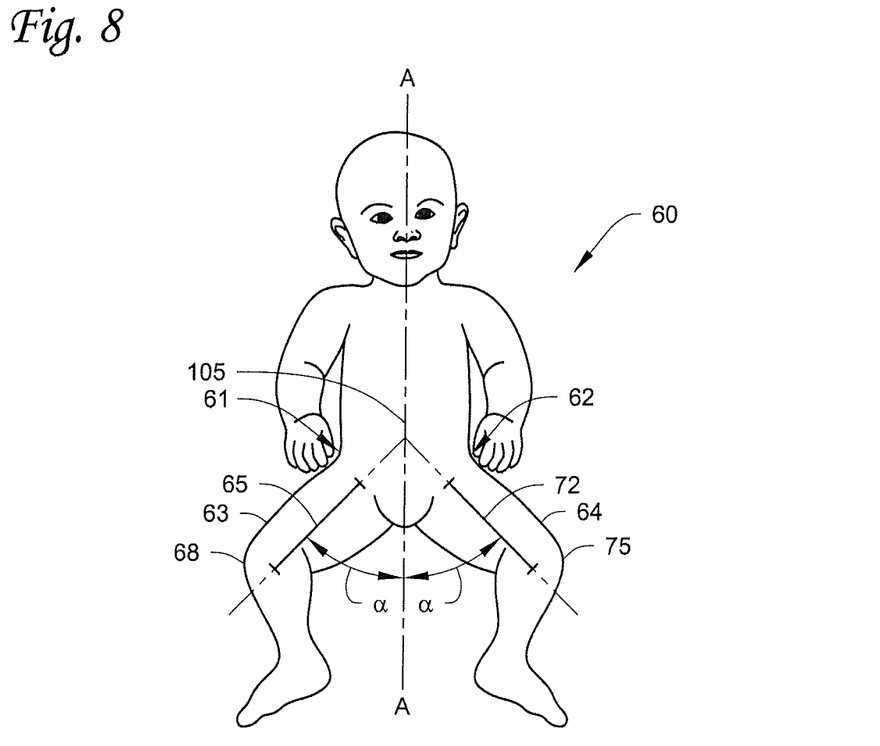
FIG. 8 is a top planar view of an infant with its thighs positioned at an abduction angle α relative to the axis A-A.
Figure 9:
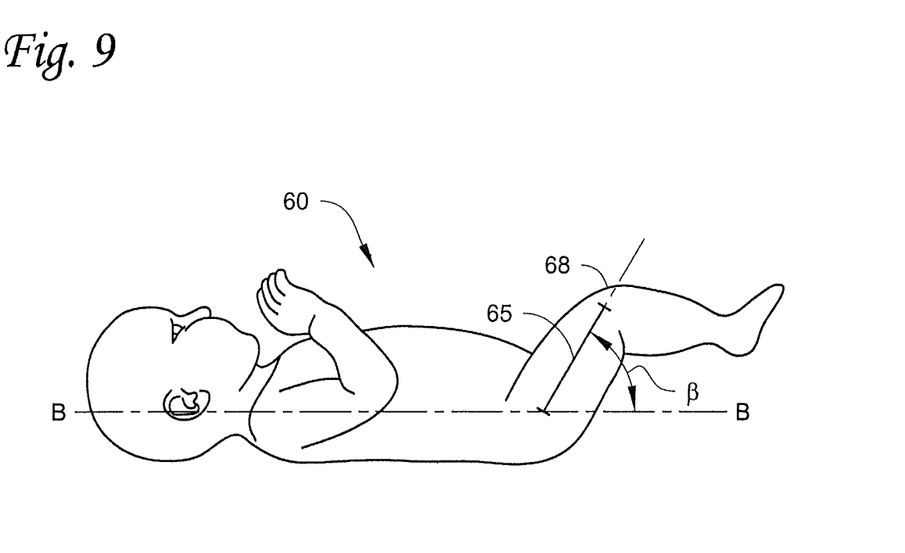
FIG. 9 is a side view of the infant of FIG. 8 with its thighs positioned at a flexion angle β relative to the axis B-B.

Another embodiment of a device that is configured to maintain an infant's thighs at an abduction angle α and a flexion angle β is illustrated by way of FIGS. 8 and 9. FIG. 8 illustrates the abduction angle α of the infant's thighs while FIG. 9 illustrates the flexion angle β of the infant's thighs. The term "infant" herein means a human child that is about 0 to about 6 months of age. The term "thigh" herein means a portion of the leg between around the hip and around the knee. While the disclosed device is described in terms of children, the disclosed device may be suitable for use in adults, such as adults suffering from hip injuries or senior citizens.

FIG. 8 shows a top view of an infant 60 having a right hip 61, a left hip 62, a right leg 63, a left leg 64 and an axis A-A. In FIG. 8, the axis A-A is shown to be vertical, and in general, extends along a spinal column (not shown) of the infant 60. The right leg 63 includes a right thigh 65 and a right knee 68, and the left leg 64 includes a left thigh 72 and a left knee 75. The right thigh 65 is a portion of the right leg 63 that extends between around the right hip 61 and around the right knee 68. The left thigh 72 is a portion of the left leg 64 that extends between around the left hip 62 and around the left knee 75.

As shown in FIG. 8, the right thigh 65 is positioned at the abduction angle α relative to the axis A-A and the left thigh 72 is positioned at the abduction angle α relative to the axis A-A.

FIG. 9 shows a side view from the right side of the infant 60 having an axis B-B. In FIG. 9, the axis B-B is shown to be horizontal, and in general, extends along a spinal column (not shown) of the infant 60. Although not shown, a side view from the left side of the infant 60 is similar to the side view from the right side of the infant 60 as shown in FIG. 9.

The right thigh 65 and the left thigh 72 are positioned at a flexion angle β relative to the axis B-B.

In one example, the disclosed device is configured to keep the thighs 65,72 of the infant 60 positioned at the abduction angle α and the flexion angle β so as to prevent or treat hip dysplasia in the infant 60.

In one implementation, the abduction angle α is from about 40 degrees to about 50 degrees. In another implementation, the abduction angle α is about 45 degrees. In yet another implementation, the abduction angle α is 45 degrees.

In yet another implementation, the flexion angle β is from about 55 degrees to about 65 degrees. In yet another implementation, the flexion angle β is about 60 degrees. In yet another implementation, the flexion angle β is 60 degrees.

Another embodiment of a device 82 that is configured to maintain an infant's thighs at specific positions is illustrated by way of FIGS. 10-14.

Figure 10:
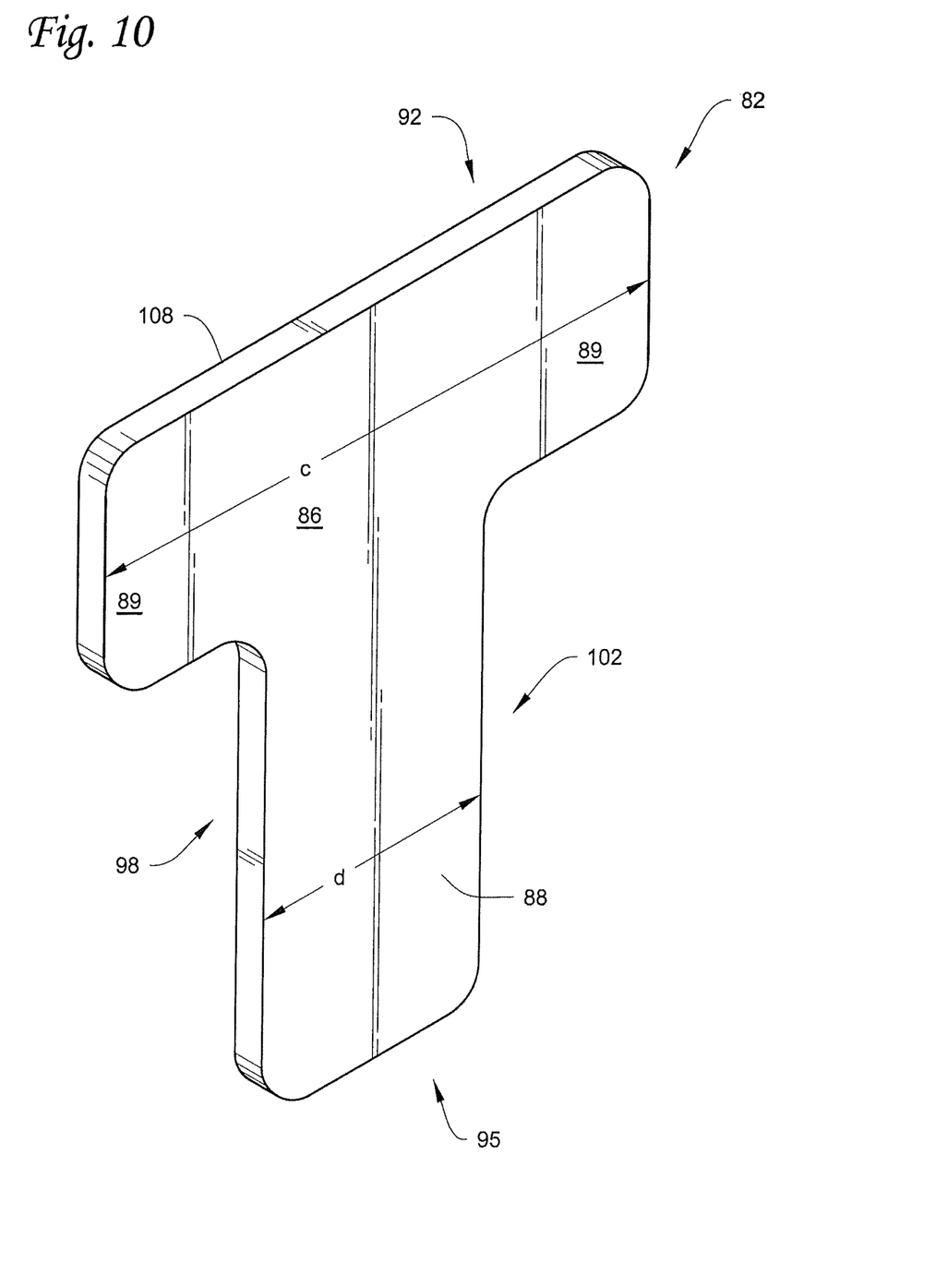
FIG. 10 is a perspective view of another embodiment of the disclosed device.
Figure 11:
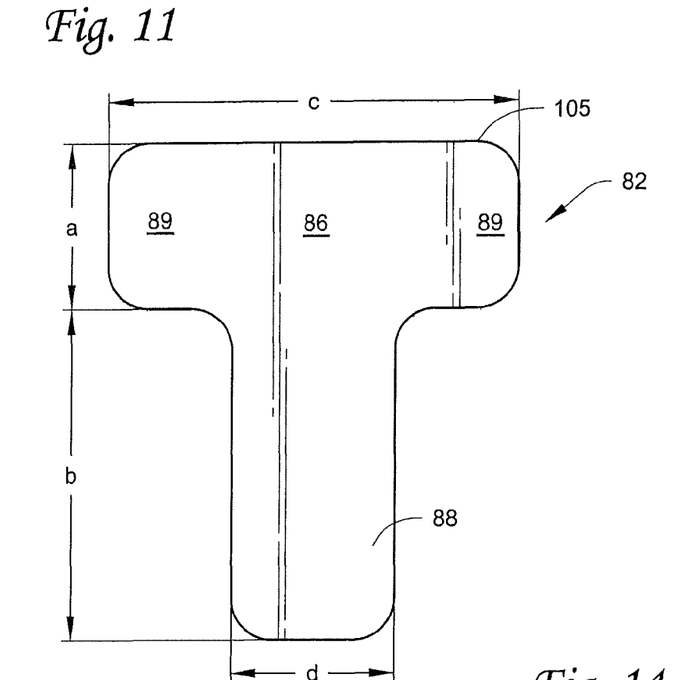
FIG. 11 is a top planar view of the disclosed device of FIG. 10. A bottom planar view of the disclosed device of FIG. 10 is identical to the top planar view shown in FIG. 11.
Figures 12, 13, 14:
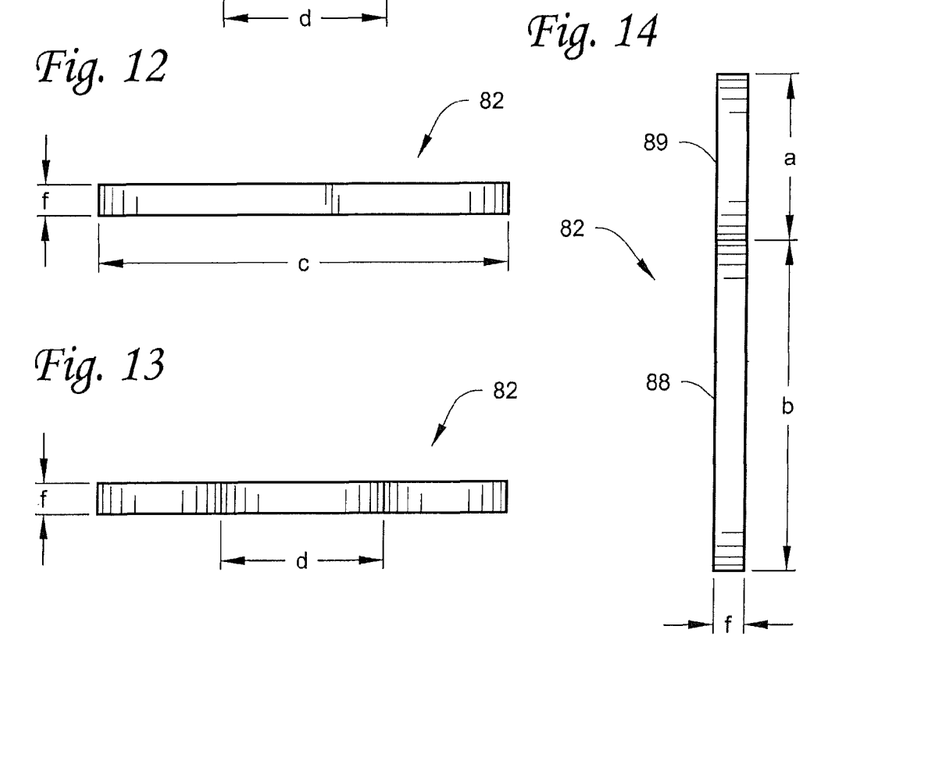
FIG. 12 is a side view from the top side of the disclosed device of FIG. 10.
FIG. 13 is a side view from the bottom side of the disclosed device of FIG. 10.
FIG. 14 is a side view from the right side of the disclosed device of FIG. 10. A side view from the left side of the disclosed device of FIG. 10 is identical to the side view from the right side shown in FIG. 14.

FIG. 10 shows a perspective view of the device 82 having a top side 92, a bottom side 95, a right side 98 and a left side 102. FIG. 11 shows a top planar view of the device 82, FIG. 12 shows a side view of the device 82 from the top side 92, FIG. 13 shows a side view of the device 82 from the bottom side 95, and FIG. 14 illustrates a side view of the device 82 from the right side 98. Although not shown, a bottom planar view of the disclosed device of FIG. 10 is identical to the top planar view shown in FIG. 11. Also, although not shown, the side view of the device 82 from the left side 102 is identical to the side view of the device 82 from the right side 98 as shown in FIG. 14.

The device 82 generally has a firmness and flexibility to keep an infant's thighs at specific positions. In one example, the device 82 has a firmness and flexibility sufficient to keep the thighs 65,72 of the infant 60 positioned at the abduction angle α and the flexion angle β so as to prevent or treat hip dysplasia in the infant 60. In another example, the device 82 has sufficient flexibility so that the device 82 can be wrapped from behind the infant's thighs 65,72 to near a navel area 105 of the infant 60 (see FIG. 8).

The device 82 is made of a material suitable for use with an infant. In one example, the device 82 is made of material that can withstand normal wash and dry temperatures. In another example, the material is non-porous so as to not to soak up fluids. In yet another example, the material is a non-porous foam material. In one implementation, the foam material is ethylene vinyl acetate. In one instance, the foam material is a one to two pound foam.

As shown in FIGS. 10 and 11, the device 82 is generally T-shaped, and includes a base portion 86. The base portion 86 has outwardly extending end portions 89. The base portion 86 further has a downwardly extending, generally central portion 88. The end portions 89 and the central portion 88 are dimensioned for keeping an infant's thighs at specific positions. In one example, the end portions 89 and the central portion 88 are dimensioned for keeping the thighs 65,72 of the infant 60 positioned at the abduction angle α and the flexion angle β so as to prevent or treat hip dysplasia in the infant 60.

In FIGS. 11 and 14, the end portions 89 are shown to have a height a and the central portion 88 is shown to have a height b. In one example, b≥a. In another example, b has a value sufficient to allow the central portion 88 to wrap the infant 60 from behind the infant's thighs 65,72 to near the navel area 105 of the infant 60. In one instance, b is from about four to about twenty inches and a is from about three to about five inches.

With reference to FIGS. 10-13, a top end 108 of the device 82 is shown to have a width c and the central portion 88 is shown to have a width d. In one example, c>d. In one instance, c is from about six to about ten inches and d is from about four to about six inches.

In FIGS. 12-14, the device 82 is shown to have a thickness f. In one example, the thickness f is from about a half an inch to about two inches.

While FIGS. 10-14 and the associated description illustrate the device 82 as being T-shaped, the device 82 can have other shapes that are suitable for achieving similar functions as described above for the device 82.

In another example, the device 82 can include an opening to facilitate air flow. In yet another example, the device 82 includes a plurality of openings. In yet another example, the device 82 includes a number of openings sufficient to keep an infant cooler and drier as compared to when there are no openings in the device 82.

In use, the central portion 88 is wrapped from behind the thighs 65,72 of the infant 60 to near the naval area 105 of the infant 60.

The device 82 can be secured to the infant 60 by any attaching device that is suitable for use with an infant. In one example, the attaching device is a strap or straps. In another example, the attaching device is a diaper.

One of the advantages of the device 82 is that the device 82 allows the infant 60 to remain supine, and yet gently keeps the thighs 65,72 of the infant 60 at a desired position to prevent or treat hip dysplasia. These features can reduce the incidence of sudden infant death syndrome.

With reference to FIGS. 15-18, a hip-aid assembly 200 including the device 82 for maintaining an infant's thighs 65,72 at specific positions is described. The hip-aid assembly 200 provides an illustration of one mechanism for securing the device 82 to the infant 60.

Figure 15:
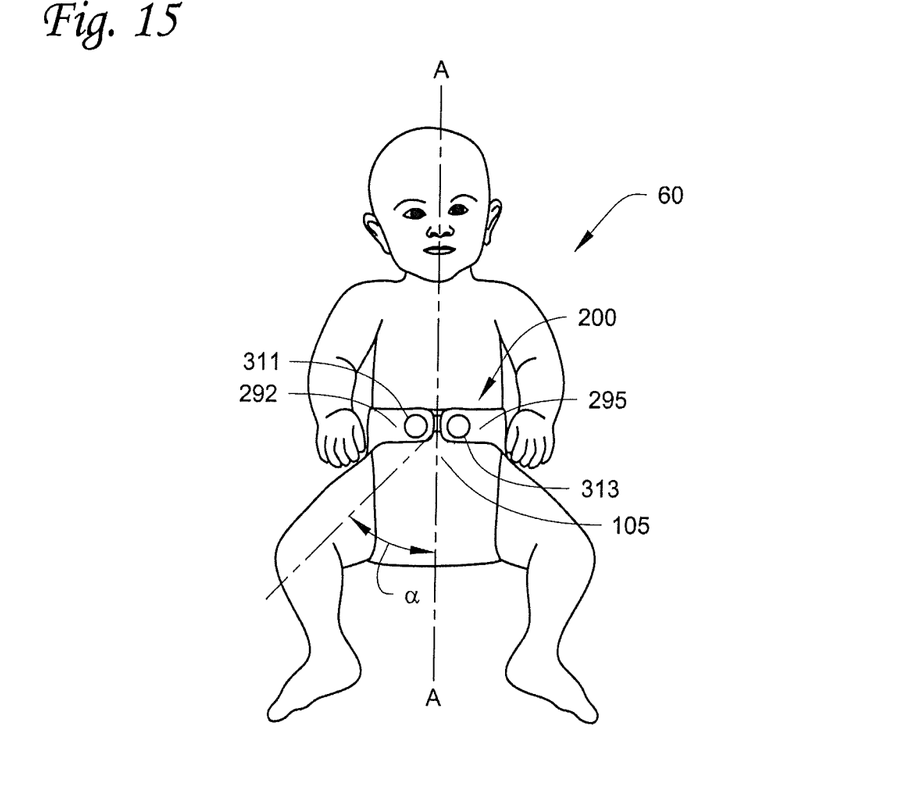
FIG. 15 is a top planar view of the hip-aid assembly including the disclosed device of FIG. 10 in use by an infant.
Figure 16:
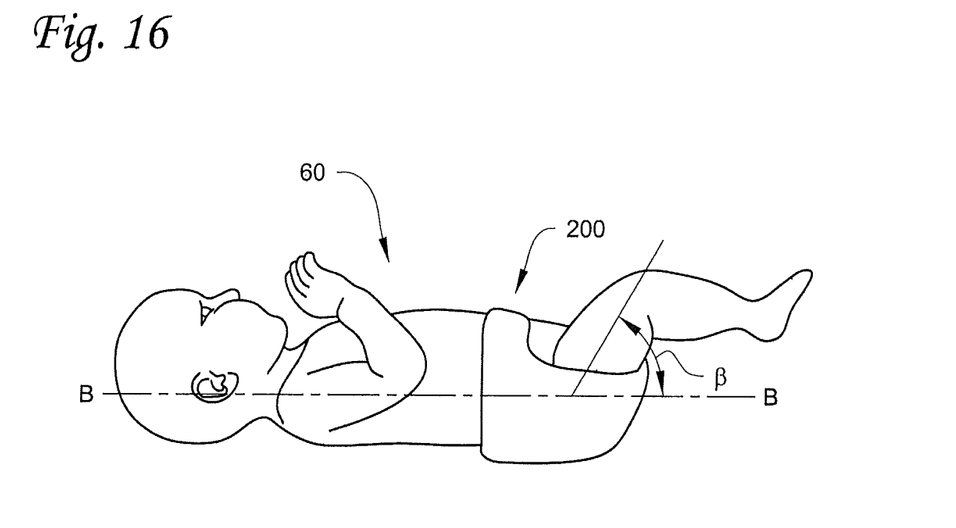
FIG. 16 is a side view of the infant of FIG. 15.
Figure 17:
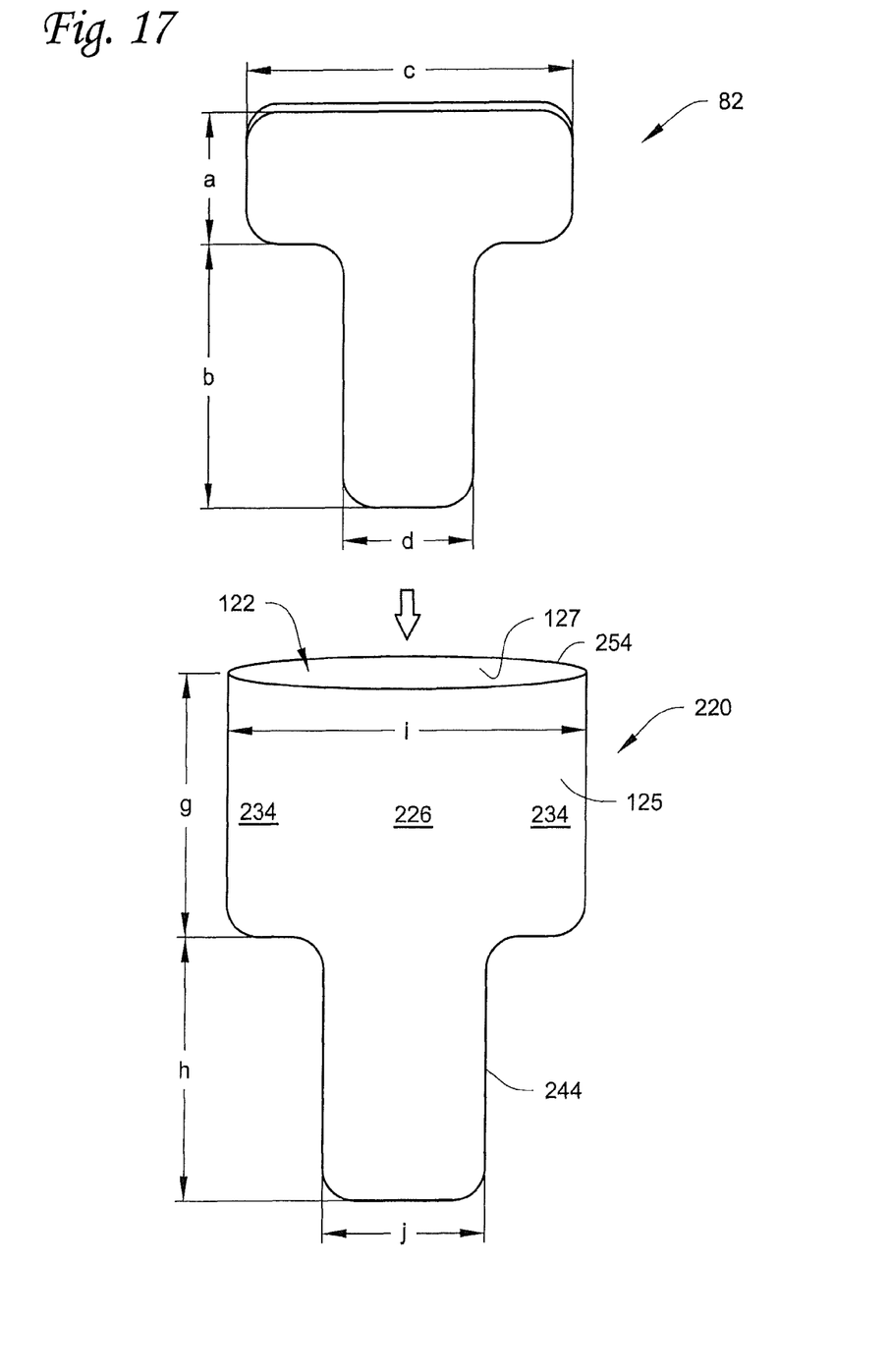
FIG. 17 is an exploded perspective view of the device of FIG. 10 and the disclosed pouch-insert.
Figure 18:
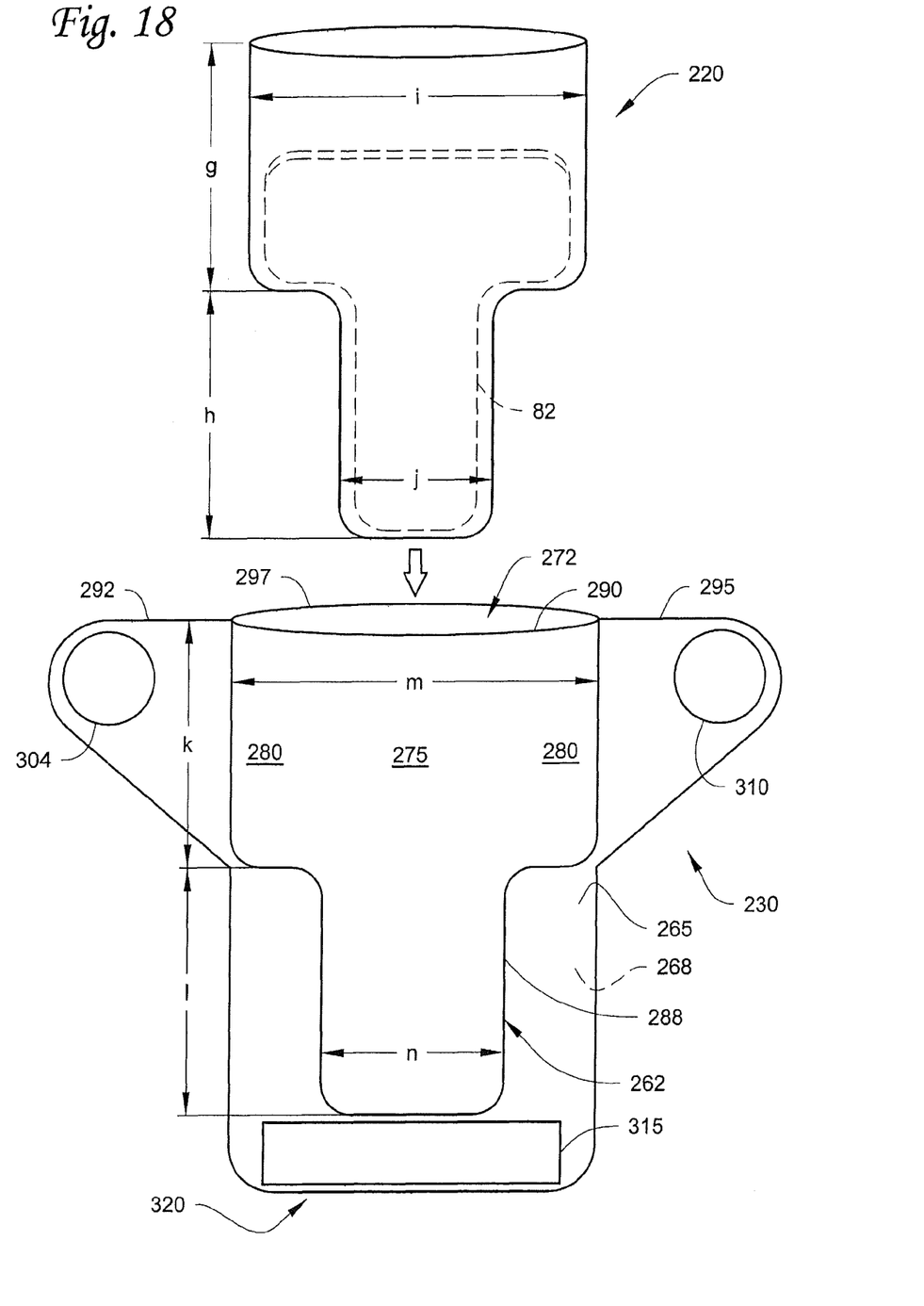
FIG. 18 is an exploded perspective view of the pouch-insert of FIG. 17 and the disclosed cover.

FIGS. 15 and 16 illustrate the hip-aid assembly 200 in use by the infant 60. FIGS. 17 and 18 illustrate the components of the hip-aid assembly 200. The hip-aid assembly 200 includes the device 82, a pouch-insert 220 and a cover 230.

With reference to FIG. 17, the pouch-insert 220 is configured to house the device 82, and has an opening 122 for the device 82 to be inserted. FIG. 18 illustrates the device 82 inserted inside the pouch-insert 220 (the dotted lines show the outline of the device 82).

The pouch-insert 220 is made of a material suitable for use with an infant. In one example, the pouch-insert 220 is made of material that can withstand normal wash and dry temperatures. In another example, the pouch-insert 220 is made of material that allows air movement in and out of the pouch-insert 220. In one example, the material is a mesh fabric. In one instance, the material of an outer layer 125 of the pouch-insert 220 is nylon and the material of an inner layer 127 of the pouch-insert 220 is a poly fiber.

The pouch-insert 220 includes a base portion 226. The base portion 226 has outwardly extending end portions 234. The base portion 226 further has a downwardly extending, generally central portion 244. The end portions 234 have a height g and the central portion 244 has a height h. In one example, the height g of the pouch-insert 220 is greater than the height a of the device 82. In another example, the height h is greater than the height b of the device 82. These features allow a smoother transition under the infant's rear and back, and also help to flex the foam material of the device 82.

In FIG. 17, a top end 254 of the pouch-insert 220 is shown to have a width i and the central portion 244 is shown to have a width j. In one example, the width i of the pouch-insert 220 is greater than the width c of the device 82 and the width j of the pouch-insert 220 is greater than the width d of the device 82 so as to allow the device 82 to be fitted inside the pouch-insert 220.

With reference to FIG. 18, the pouch-insert 220 can be inserted inside a cover 230. The cover 230 has a front side 265 and a back side 268. FIG. 18 shows the front side 265 of the cover 230.

The cover 230 is made of a material suitable for use with an infant. In one example, the material is cotton, polyester or a blend of cotton and polyester. In another example, the back side 268 of the cover 230 is made of cotton, polyester or a blend of cotton and polyester and the front side 265 of the cover 230 is made of a synthetic moisture wicking material.

In one example, the cover 230 includes a pocket 262 on the front side 265 as shown in FIG. 18. The pocket 262 is configured to allow the pouch-insert 220 to be inserted inside the pocket 262. The pocket 262 includes an opening 272 that is sized to allow the pouch-insert 220 to be inserted.

The pocket 262 includes a base portion 275. The base portion 275 has outwardly extending end portions 280. The base portion 275 further has a downwardly extending, generally central portion 288. The end portions 280 have a height k and the central portion 288 has a height l. In one example, the height k of the pocket 262 is equal to or greater than the height g of the pouch-insert 220. In another example, the height l of the pocket 262 is greater than the height h of the pouch-insert 220. In yet another example, a top end 290 of the pocket 262 has a width m and the central portion 288 of the pocket 262 has a width n. In one implementation, the width m of the pocket 262 is greater than the width i of the pouch-insert 220 and the width n of the pocket 262 is greater than the width j of the pouch-insert 220 so as to allow the pouch-insert 220 to be fitted inside the pocket 262.

The cover 230 also has outwardly extending wings 292, 295 on a top end side 297 of the cover 230. In one example, fasteners 304,310 are provided on the wings 292,295 on the front side 265 of the cover 230. In another example, fasteners 311,313 also are provided on the wings 292,295 on the back side 268 of the cover 230 as shown in FIG. 15. In yet another example, a fastener 315 is provided on a bottom edge 320 on the front side 265 of the cover 230. In yet another example, a fastener (not shown) is provided on the bottom edge 320 on the back side 268 of the cover 230.

The fastener utilized can be any securing device commonly used in the garment industry, or may be any type of securing device that would provide secure yet releasable attachment to the user. The fastener utilized can be a hook-and-loop fastener, buttons, zipper, push buttons, pins, etc., or any combination thereof.

In use, the central portion 288 is wrapped from behind the thighs 65,72 of the infant 60 to near the naval area 105 of the infant 60 as shown in FIGS. 15 and 16. In one example, the hip-aid assembly 200 is secured to the infant 60 by the fasteners 304,310 connecting with the fastener (not shown) on the bottom edge 320 on the back side 268 of the cover 230. In another example, the hip-aid assembly 200 can be secured to the infant 60 by the fastener 315 connecting with the fasteners 311,313. In yet another example, the wings 292,295 can overlap so that the fasteners 304,310 can connect with the respective fasteners 311,313 so as to allow a snugger fit.

In yet another embodiment, the pouch-insert 220 is molded on the cover 230.

In yet another embodiment, the hip-aid assembly 200 further includes a diaper (not shown). In yet another embodiment, the hip-aid assembly further includes a removable liner (not shown).

In one embodiment of the disclosed method, the disclosed method includes keeping the thighs 65,72 of the infant 60 positioned at the abduction angle α and the flexion angle β for an amount of time sufficient to prevent or treat hip dysplasia in the infant 60. In one example, the amount of time is from about two days to about two years. In another example, the amount of time is from about six to about eighteen weeks. In yet another example, the amount of time is full-time from about six to about twelve weeks and part-time from about four to about six weeks. In one instance, full-time is an amount of time other than bathing and diaper changes. In another instance, part-time is during the night.

In one implementation, the disclosed method involves the use of the device 82 for keeping the thighs 65,72 of the infant 60 positioned at the abduction angle α and the flexion angle β for an amount of time sufficient to prevent or treat hip dysplasia in the infant 60.

The above specification, examples and data provide a complete and enabling description of the claimed invention. Since many embodiments can be made without departing from the spirit and scope of the claimed invention, the invention resides in the claims hereinafter appended.

The invention claimed is:

1. A hip-positioning assembly that, when worn by an infant, stabilizes hip joints of the infant, comprising:
    a flexible base portion having a pair of opposed, outwardly extending end portions dimensioned for supporting thighs of the infant at an acute angle greater than zero relative to a dorsal plane of the infant, with knees of the infant in a flexed position; and a downwardly extending, generally central portion adapted for positioning between the infant thighs and dimensioned for retaining the infant thighs in an abducted position;
    the base portion has a firmness and a flexibility sufficient to retain an infant's thighs at an abduction angle and a flexion angle;
    the end portions and the central portion are a unitary single-piece construction of a non-porous foam material, and the base portion is a single piece of the non-porous foam material;
    the base portion has a first width at the end portions, the central portion has a second width; and the first width is greater than the second width;
    the end portions have a first height, and the central portion has a second height and the second height is greater than or equal to the first height;
    a pouch-insert that is sized to permit the base portion to fit completely therein; the pouch-insert is made of fabric and includes an opening that permits insertion of the base portion therein; and the pouch-insert includes a first portion with outwardly extending portions configured to receive the end portions of the base portion, and a downwardly extending second portion configured to receive the central portion of the base portion;
    the first portion of the pouch-insert has a width that is greater than the first width;
    the first portion of the pouch-insert has a height that is greater than the first height;
    the downwardly extending second portion has a width that is greater than the second width; and
    the downwardly extending second portion has a height that is greater than the second height.

2. The hip positioning assembly of claim 1, wherein the base portion is generally T-shaped.

3. The hip positioning assembly of claim 1, wherein the first height is between about 3-5 inches, and the second height is between about 4-20 inches.

4. The hip positioning assembly of claim 1, wherein the first width is between about 6-10 inches, and the second width is between about 4-6 inches.

5. The hip positioning assembly of claim 1, further comprising one or more openings in the base portion.

6. The hip positioning assembly of claim 1, further comprising a cover that is configured to house the entire pouch-insert therein.

7. A hip-positioning assembly for an infant comprising:
    a flexible base portion having a pair of opposed, outwardly extending end portions dimensioned for supporting thighs of an infant at an acute angle greater than zero relative to a dorsal plane of the infant, with knees of the infant in a flexed position; and a downwardly extending, generally central portion adapted for positioning between the infant thighs and dimensioned for retaining the infant thighs in an abducted position;
    the end portions and the central portion are a unitary single-piece construction of a non-porous material;
    the end portions define a first width of the flexible base portion, and the central portion defines a second width of the flexible base portion, and the first width is greater than the second width;
    the end portions of the flexible base have a first thickness and the central portion has a second thickness, and the first thickness is equal to the second thickness; and
    a pouch-insert that is sized to permit the flexible base portion to fit completely therein; the pouch-insert is made of fabric and includes an opening that permits insertion of the flexible base portion therein; and the pouch-insert includes a base portion with outwardly extending portions configured to receive the end portions of the flexible base portion, and a downwardly extending central portion configured to receive the central portion of the flexible base portion.

8. The hip positioning assembly of claim 7, further comprising a cover that is configured to house the pouch-insert.

9. The hip positioning assembly of claim 7, wherein the non-porous material is foam.

* * * * *